United States Patent
Preiss et al.

(10) Patent No.: US 6,313,347 B1
(45) Date of Patent: Nov. 6, 2001

(54) METHOD FOR PRODUCING VINYL OXIME-ETHERS

(75) Inventors: Thomas Preiss, Ludwigshafen; Jochem Henkelmann, Mannheim, both of (DE); Boris Trofimov, Irkutsk (RU); Albina Mikhaleva, Irkutsk (RU); Alexander M. Vasiltsov, Irkutsk (RU)

(73) Assignee: BASF Aktiengesekkschaft, Ludwigshafen (DE)

( * ) Notice: Subject to any disclaimer, the term of this patent is extended or adjusted under 35 U.S.C. 154(b) by 0 days.

(21) Appl. No.: 09/744,246

(22) PCT Filed: Jul. 23, 1999

(86) PCT No.: PCT/EP99/05292

§ 371 Date: Jan. 30, 2001

§ 102(e) Date: Jan. 30, 2001

(87) PCT Pub. No.: WO00/07983

PCT Pub. Date: Feb. 17, 2000

(30) Foreign Application Priority Data

Jul. 31, 1998 (DE) ............................................... 198 34 654

(51) Int. Cl.$^7$ .................................................. C07C 249/00
(52) U.S. Cl. ............................................................ 564/256
(58) Field of Search ................................................ 564/256

(56) References Cited

FOREIGN PATENT DOCUMENTS 0 714 886    6/1996  (EP) .

OTHER PUBLICATIONS

O.A. Tarasova, et al., Chemical Abstracts, vol. 122, No. 15, pp. 863–869, "The Nucleophilic Addition to Alkynes in Superbasic Catalytic Systems V.* Vinylation of Ketozimes," 1994 (Translated from Zhurnal Organicheskoi Khimii, vol. 30, No. 6, pp. 810–815, Jun. 1994. Original article submitted Apr. 12, 1994).

V.P. Pivnenko, et al., Chemical Abstracts, vol. 81, No. 21, p. 367, AN 135371q, "Synthesis and Study of Dielectric Properties of Aliphatic–Series Vinyl Ethers," Nov. 25, 1974.

Derwent Publications, AN 94–300713, SU 1 095 593, Mar. 30, 1994.

T. Sheradsky, Tetrahedron Letters, No. 1, pp. 25–26, "The Rearrangment of O–Vinyloximes: A New Synthesis of Substituted Pyrroles," 1970.

B.A. Trofimov, et al., Irkutsk Intitute of Organic Chemistry, No. 3, p. 631, "O–Vinylaceoxime," Mar. 1979.

*Primary Examiner*—Samuel Barts
(74) *Attorney, Agent, or Firm*—Oblon, Spivak, McClelland, Maier & Neustadt, P.C.

(57) ABSTRACT

In the process for the preparation of vinyloxime ethers of the formula I

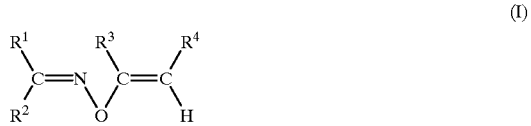

by reacting an oxime with an alkyne
where
$R^1$ and $R^2$ are identical or different and are alkyl or aryl radicals,
$R^3$ is hydrogen, an alkyl or aryl radical, and
$R^4$ is a radical having the meaning of $R^3$, which may be different than $R^3$, or is a hydroxyalkyl radical,
in a superbasic polar organic solvent in the presence of a strong base, the reaction is carried out under conditions such that the resulting vinyloxime ether stays in contact with the other constituents of the reaction mixture for only a short time so that it is unable to decompose or react to give secondary products to a significant extent.

7 Claims, 2 Drawing Sheets

METHOD FOR PRODUCING VINYL OXIME-ETHERS

This application is a 371 of PCT/EP99/05292 filed Jul. 23, 1999. The invention relates to a process for the preparation of vinyloxime ethers by reacting ketoximes with alkynes.

It is known to react dimethyl acetylenedicarboxylate in the presence of a basic catalyst with ketoximes to give O-vinyloxime ethers (T. Sheradsky, Tetrahedron Letters 1970, No. 1, P. 25–26).

It is further known to react acetone oxime with acetylene in dimethyl sulfoxide to give O-vinylacetone oxime (Trofimov, Izv. Akad. Nauk SSSR, Ser. Khim, 1979, No. 3, p. 695). The yields are up to 10%.

In Russ. J. Org. Chem. Vol. 30 (1994), No. 6, pages 810 to 815, Tarasova et al. describe the reaction of ketoximes with acetylene in dimethyl sulfoxide in the presence of potassium hydroxide to give O-vinyloxime ethers. Yields of from 10 to 72% are achieved. For higher yields, reaction times up to 6 hours are required. In this connection, it is necessary to interrupt the reaction several times in order to remove the desired product from the mixture since the desired vinyloxime ether, when left in the reaction mixture for a prolonged time, reacts further with ring closure to give the corresponding pyrrole.

It is an object of the present invention to carry out the known reaction of ketoximes with alkynes, in particular acetylene, such that the O-vinyloxime ethers are obtained in a higher overall yield at higher space-time yields with the formation of fewer by-products, in a form which is accordingly more pure or is easier to purify.

The invention proceeds from a process for the preparation of vinyloxime ethers of the formula I

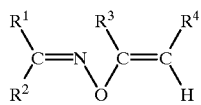
(I)

by reacting a ketoxime of the formula II

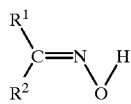
(II)

with an alkyne of the formula III

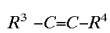
(III)

where $R^1$ and $R^2$ are identical or different and are alkyl or aryl radicals, $R^3$ is hydrogen, an alkyl or aryl radical, and $R^4$ is a radical having the meaning of $R^3$, which can be different than $R^3$, or is an hydroxyalkyl radical, in a superbasic polar organic solvent in the presence of a strong base.

The novel process comprises carrying out the reaction under conditions such that the vinyloxime ether formed stays in contact with the other constituents of the reaction mixture for only a short time so that it is unable to decompose or react to give secondary products to a significant extent.

A simple way of limiting the contact time involves interrupting the reaction after just a short time, for example by cooling. This may result in the ketoxime used being converted only incompletely. In this case, the reaction product must be separated off from the other constituents of the mixture, and such constituents must be returned to the reaction zone. This relatively laborious procedure is generally more than compensated for by the fact that the significantly fewer by-products form compared with the amount of product.

The abovementioned reaction time is dependent on a number of parameters, such as temperature, pressure, nature of the superbasic solvent, of the base and of the reactants used etc. As explained below, in each individual case simple experiments can be used to ascertain the dependency of the reaction on the reaction time, meaning that in each specific case it is possible to find the optimum reaction time in relation to the yield. Although it is not possible here to give values which are generally applicable for the reaction times, the optimum values at the preferred temperatures and pressures are in most cases between 10 seconds and 1 hour, preferably between 1 and 30 minutes.

The reaction of ketoxime with alkyne can be carried out at room temperature or at elevated temperature. The reaction temperature is also dependent in individual cases on the nature of the reactants. While some combinations of reactants react quickly enough only at relatively high temperatures, above 50° C., say in the range from 60 to 125° C., in other cases the reaction products are no longer stable at temperatures in this range and tend to decompose. In most cases the most favorable reaction temperatures are in the range from 50 to 100° C., preferably from 65 to 85° C.

The reaction can be carried out under atmospheric pressure or under increased pressure. In general, higher pressures are advantageous. They can be in the range from more than 1 to 50 bar, preferably from 10 to 40 bar.

According to an advantageous embodiment of the process, the vinyloxime ether formed is removed from the reaction mixture during the reaction. This can be done in various ways. In a very simple manner, the reaction product can be separated off from the mixture with the other constituents by carrying out the reaction in an inert nonpolar organic solvent which is immiscible with the superbasic polar solvent and which is a good solvent for the resulting O-Vinyloxime ether. In this case, the reaction product is distributed between the polar and the nonpolar solvent phase, the majority going into the nonpolar phase, depending on the type of solvent. Here, it is not in direct contact with the other constituents, particularly with the strong base, and, under these conditions, has a significantly lower tendency to decompose or to react further to give undesired secondary products such as polymers or pyrrole derivatives.

Another method of separation involves driving out the vinyloxime ether formed from the reaction mixture by evaporation. The resulting mixture of vaporous vinyloxime ether and alkyne, for example acetylene, is then expediently separated into its constituents, and the alkyne is returned to the reaction zone. This procedure is naturally particularly suitable for continuous operation.

The nonpolar organic solvents used are preferably hydrocarbons, particularly preferably saturated aliphatic hydrocarbons. The nonpolar solvent should expediently have a boiling point under atmospheric pressure in the range from about 25 to 200° C., preferably from 30 to 100° C. It is essential that the nonpolar organic solvent is immiscible with the superbasic organic solvent, but is a good solubilizer for the vinyloxime ether formed. It is also possible to use mixtures of nonpolar organic solvents. A particularly preferred example is n-pentane.

According to general language usage, the superbasic organic solvent is a solvent of high polarity which is suitable for forming carbanions by deprotonating other compounds. Examples are dimethyl sulfoxide, sulfolane (tetramethylene sulfone) an hexamethylphosphor amide. The concentration of the oxime used in the reaction solution likewise has a significant effect on the yield. In general, the yield decreases with increasing starting concentration of oxime. Conversely, the amount of solvent volumes to be handled increases with dilution, thus increasing the cost of the process. Also, too dilute a solution may result in the reaction time being longer. In general, starting concentrations are chosen in the range from about 4 to 20% by weight, preferably from 6 to 15% by weight it can also be expedient to use only some of the oxime at the start of the reaction and to add the remainder during the course of the reaction. In this procedure it is possible to manage with smaller amounts of solvent.

For the purpose of the novel process, strong bases are, in particular, inorganic bases, preferably hydroxide. The hydroxides of the alkali metals and alkaline earth metals, particularly of the alkali metals, are generally preferred.

The strong base can be used in stoichiometric or substoichiometric amounts relative to the ketoxime. It is also possible to use amounts which are greater than the stoichiometric amounts. An unreacted excess of base generally remains in the reaction mixture, i.e. undissolved in the polar superbasic solvent, where it is unable to adversely affect the constituents of the reaction mixture, particularly the reaction product. Since an excess of base has no effect on the reaction, the deliberate use of an excess is usually avoided. A deficit of base, e.g. an amount of only from 80 to 90% of the stoichiometric amount is in many cases sufficient for complete conversion. It is also possible, and in some cases advantageous, to react base and oxime beforehand to give the alkali metal oximate and to add this to the reaction mixture.

If, in the formulae, $R^1$, $R^2$, and $R^3$ and $R^4$ are alkyl radicals, they preferably have from 1 to 4 carbon atoms; the same is true of hydroxyalkyl radicals $R^4$. If $R^1$ to $R^4$ are aryl radicals, they are usually monocyclic; they may optionally have up to three substituents, for example halogen atoms, lower alkyl or alkoxy radicals.

Compounds in which $R^3$ and optionally also $R^4$ is a hydrogen atom are particularly preferred, as are compounds in which $R^1$ and $R^2$ are aliphatic radicals or in which one of these radicals is aliphatic and the other is aromatic.

In the novel process, the addition of water should be avoided if at all possible since it considerably reduces the yield of O-vinyloxime. Even the usual content of water in the alkali metal hydroxide or in the corresponding base causes this to happen to some extent, but can generally be tolerated. It is also unnecessary to remove the water formed during the oximate formation from base and oxime from the equilibrium, e.g. by distillation, as is frequently the case in the preparation of vinyl ethers.

BRIEF DESCRIPTION OF DRAWINGS

The attached diagrams (FIGS. 1, 2 and 3) illustrate the effect of various parameters on the course of the reaction or on the yield of O-vinylacetone oxime.

In FIG. 1, the yield (Y) of O-vinylacetone oxime in percent, based on acetone oxime, is given on the ordinate, and the starting concentration (A) of acetone oxime in the reaction solution is given in percent on the abscissa.

In FIG. 2, the reaction time (R) in hours is given on the abscissa, and the yield (Y) in percent is given on the ordinate. The values apply to the conversion of acetone oxime in give O-vinylacetone oxime at from 72 to 75° C. and under a pressure of 15 bar. As can be seen, particularly favorable yields are achieved after a reaction time of approximately just 10 minutes. The drop in the yields after relatively long reaction times is accompanied by an increase in the formation of secondary product and by-products.

In FIG. 3, the reaction temperatures (T) is ° C. is given on the abscissa, and the yield (Y) in percent is given on the ordinate. In other respects, the reaction conditions are the same as in FIG. 2.

Figure 1:
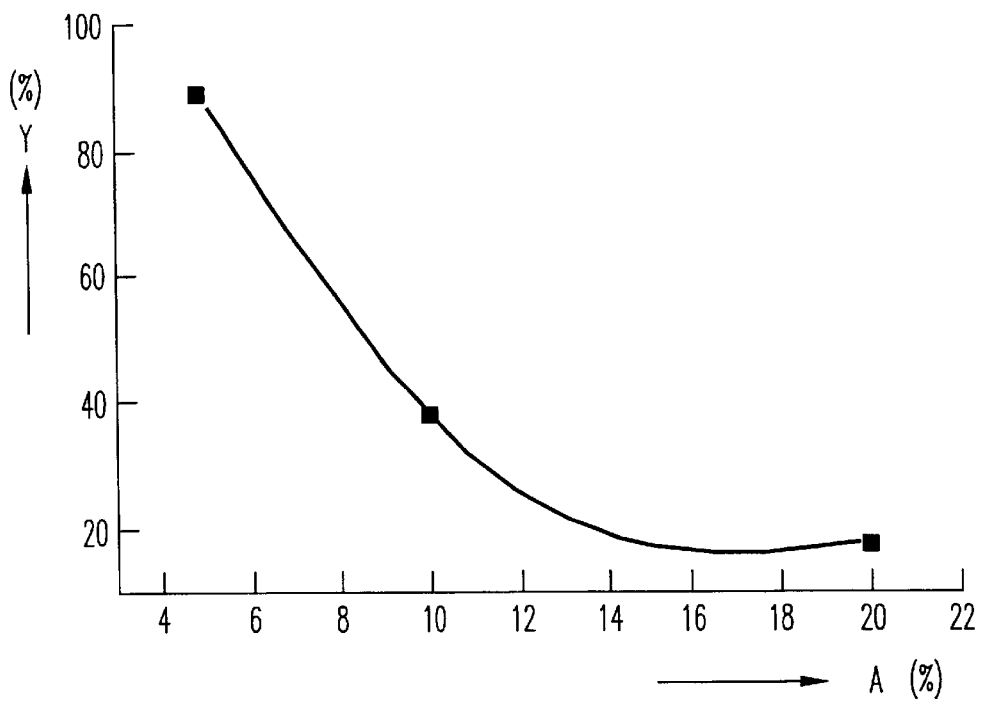
FIG. 1 shows the dependency of the yield (Y) of O-vinylacetone oxime in percent of the starting concentration (%) of acetone oxime.
Figure 2:
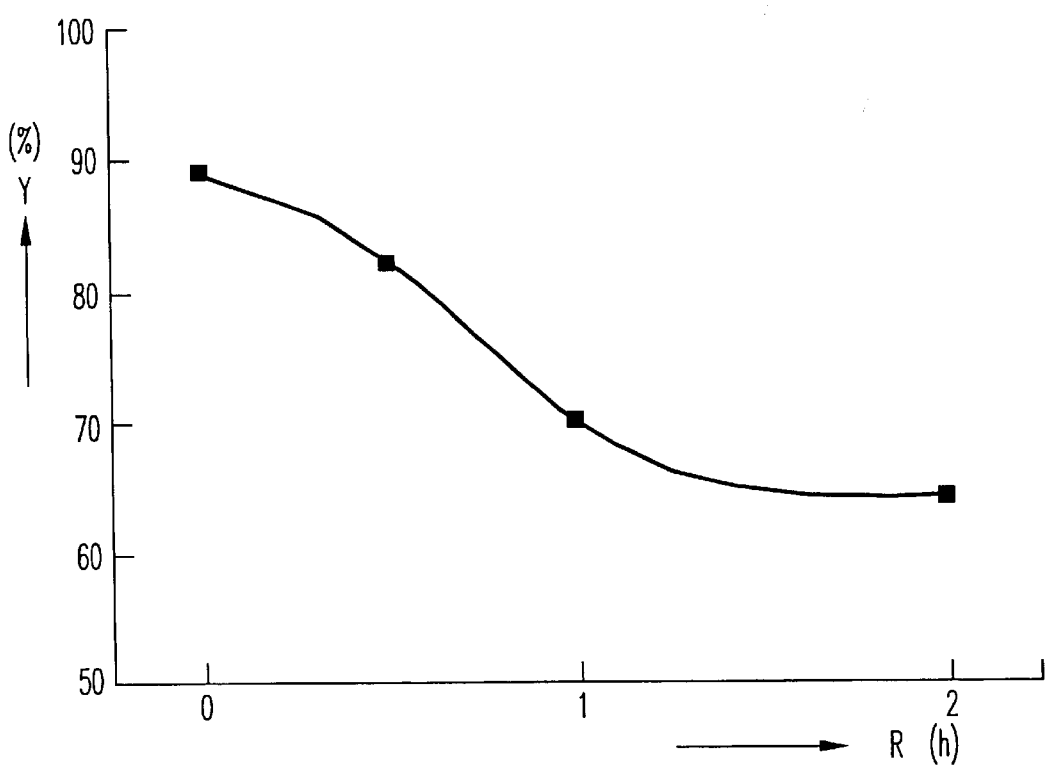
FIG. 2 shows the dependency of the yield (Y) on the reaction time at increased pressure (15 bar) and elevated temperature (72 to 75° C.).
Figure 3:
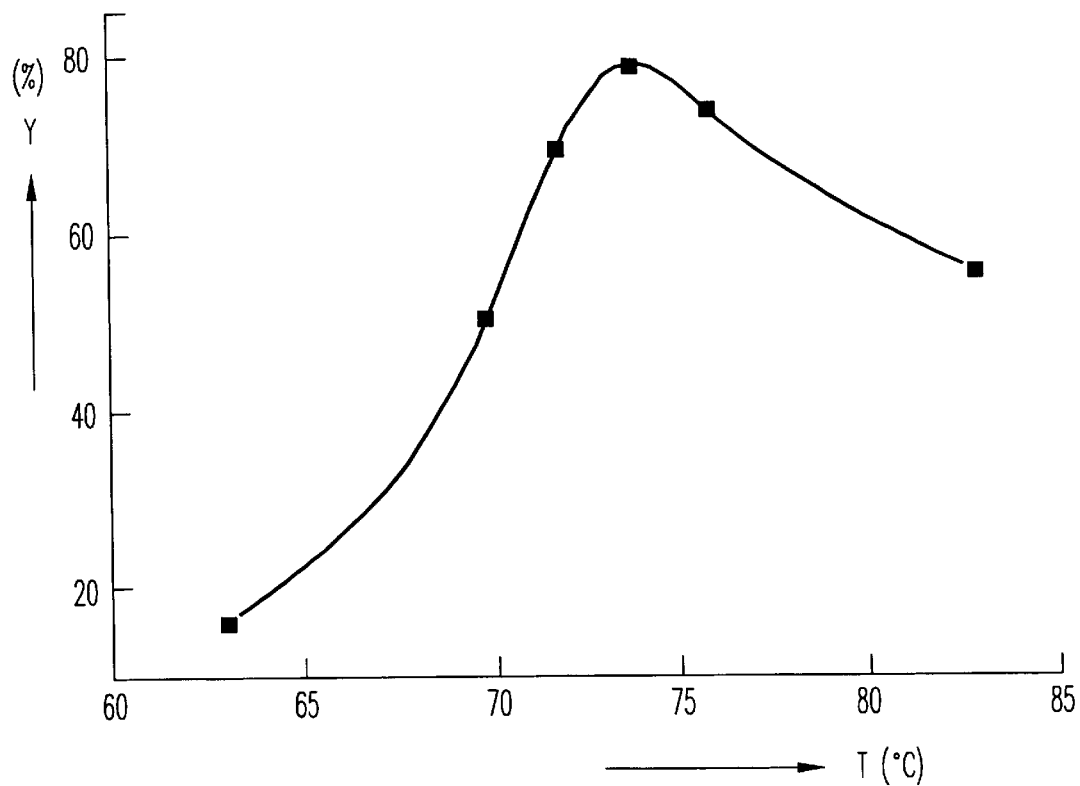
FIG. 3 shows the dependency of the yield (Y) of O-vinylacetone oxime (%) on the reaction temperature.

The O-vinyloxime ethers obtained by the novel process are used widely in known manner, especially for the preparation of co- and homopolymers, e.g. of polyvinyloxime ethers.

The examples below illustrate preferred embodiments of the novel process. Unless stated otherwise, amount ratios and percentages are in units by weight.

The examples show that the best yields are obtained with unsubstituted acetone oxime and acetylene, i.e. the higher aliphatic and in particular the aromatic ketoximes produce significantly lower yields of vinyloxime ethers. All of the experiments were carried out in individual batches—normally in autoclaves. They have been conceived and are to be understood as demonstration experiments for the basic functioning of the process. It is of course possible here to carry out the process continuously on an industrial scale, in which case the reaction mixture is passed through a reaction zone of a suitable temperature and under suitable pressure. It is of course also possible here to have significantly shorter reaction times, which may lead to even better yields. In the case of the experiments described here, the method usually involved heating the mixture to the reaction temperature in an autoclave and keeping it at this temperature for a period of various length. The shortest reaction time including heating up and cooling down phases was assumed to be about 10 minutes. In some examples, the gas pressure was measured only at the start, i.e. prior to heating; at the reaction temperature, correspondingly higher pressures were then reached.

The amounts of starting materials, process products and by-products were determined by gas chromatography, in most cases by gas/liquid partition chromatography (GLC).

EXAMPLE 1

A 1 liter rotating steel autoclave was charged with 100 ml of pentane and a potassium oximate solution in dimethyl sulfoxide (DMSO), obtained by heating a mixture of 6.25 g (85.5 mmol) of acetone oxime, 5 g (75.5 mmol) of KOH (water content 15%) and 125 ml of DMSO to from 110 to 115° C. for 5 minutes. The mixture was saturated with acetylene under a pressure of 16 bar and heated at 72° C. for 30 minutes, a maximum acetylene pressure of about 35 bar being reached. Heating was then stopped, and the vent valve opened. After the system had cooled to room temperature, the excess acetylene which remained (residual pressure 6 bar) was released to atmospheric pressure via a receiver cooled with acetone/dry ice. The reaction mixture was removed, and the pentane layer was separated off, combined with the condensate in the receiver, washed with 2×3 ml of water, dried over calcined magnesium sulfate and analyzed by gas/liquid partition chromatography (GLC). According to this, the content of O-vinylacetone oxime was 1.56 g. The reaction mixture which was left was neutralized with dry ice and likewise analyzed by gas chromatography. As well as 3.31 g of O-vinylacetone oxime, it also comprised 2.25 g of acetone oxime (59.7% conversion). The yield of O-vinylacetone oxime was 96.4%, based on the reacted acetone oxime.

EXAMPLE 2

The process was carried out essentially as in Example 1, but the reaction temperature was 75° C. The yield was 89%, based on the acetone oxime used; unreacted acetone oxime was no longer detectable in the product by GLC.

EXAMPLE 3

The process was carried out essentially as in Example 1. The autoclave was cooled to room temperature, and the excess acetylene (residual pressure 5 bar) was released via a cold trap. The reaction mixture was removed, and the pentane phase was separated off, washed with 2×3 ml of water, dried over magnesium sulfate and analyzed by gas chromatography (GLC); the content of O-vinylacetone oxime was 2.24 g. The reaction mixture which remained was neutralized with dry ice, and the content of O-vinyl acetone oxime was determined by GLC as 4.75 g. The total yield was 6.99 g (82.6%). The reaction mixture did not contain unreacted acetone oxime.

EXAMPLE 4

Comparative Example

The process was carried out essentially as in Example 1, but the reaction temperature was 74° C., and no pentane was added. The yield of O-vinylacetone oxime was 65.9%; in addition, 14.4% of 2-methylpyrrole, based on acetone oxime, were found. No unreacted acetone oxime was detected.

EXAMPLE 5

Comparative Example

A 1 liter autoclave was charged with 12.5 g (171 mmol) of acetone oxime, 10 g (151 mmol, 85% purity) of KOH and 125 ml of DMSO. This mixture was then saturated with acetylene and adjusted to a pressure of 13 bar. The solution was heated to 75° C. over the course of 40 minutes and stirred at this temperature for a further 2 hours. After the autoclave had been cooled to room temperature, the reaction mixture was extracted with 2×20 ml of diethyl ether and with 2×20 ml of pentane. The extracts were washed with water and dried over magnesium sulfate. After filtering and distilling off the solvent, the residue was analyzed using gas chromatography (GC). 7.84 g of O-vinylacetone oxime in 82.4% purity were obtained. The yield was 38.1%.

EXAMPLE 6

A 1 liter autoclave was charged with 12.5 g (171 mmol) of acetone oxime, 10 g (151 mmol, 85% purity) of KOH, 125 ml of DMSO and 100 ml of pentane. This mixture was then saturated with acetylene and adjusted to a pressure of 10 bar. The solution was heated to 70° C. over the course of 40 minutes and stirred at this temperature for a further 100 minutes. During this time, the temperature increased to 83° C. and was then lowered again to 70° C. After the autoclave had been cooled to room temperature, the pentane phase was separated off and the DMSO phase was extracted with 2×20 ml of ether and with 2×20 ml of pentane. The combined pentane and ether phases were then dried over magnesium sulfate. Filtering off the desiccant and distilling off the solvent gave 15.1 g of O-vinylacetone oxime in a purity of 98.7%. The yield was 88%.

EXAMPLE 7

Comparative Example

A 100 ml three-necked flask was charged with 5.6 g (0.1 mol) of KOH and 50 ml of DMSO. The mixture was heated to from 95 to 97° C. and saturated with acetylene. After 15 minutes, 7 g (96 mmol) of acetone oxime in 20 ml of DMSO were then added to the mixture dropwise over the course of 4 hours. The solution was then gassed with acetylene for a further 2 hours. The vinyloxime either formed was collected in a cold trap at −78° C. 5.52 g of O-vinylacetone oxime in 89% purity were collected. The yield was 51%.

EXAMPLE 8

A 1 liter rotating steel autoclave was charged with a potassium oximate solution which had been obtained by heating a mixture of 6.25 g (85.5 mmol) of acetone oxime, 5 g (75.5 mmol) of KOH (water content 15%) in 125 ml of DMSO at from 110 to 115° C. for 5 minutes. The mixture was saturated with acetylene to a pressure of 16 bar and heated at 72° C. for 30 minutes. Immediately after heating had finished, the vent valve was opened, the autoclave was left to cool to room temperature and emptied, and the reaction mixture was neutralized with dry ice. Contents of 7.06 g of O-vinylacetone oxime (83.4% yield) and 0.55 g of 2-methylpyrrole (7.9%) were determined by GLC.

EXAMPLE 9

The process was carried out essentially as described in Example 8, However, a potassium oximate solution in 125 ml of DMSO was used, prepared from 9.85 g (85.6 mmol) of pinacolone oxime (3,3-dimethyl-2-butanone oxime) and 5.64 g (85.6 mmol) of KOH. The mixture was heated at 70° C. in an autoclave for about 10 minutes. 86% of the pinacolone oxime used were converted. The yield of O-vinylpinacolone oxime was 81%, based on reacted pinacolone oxime. 1.9% of pinacolone (on the same basis) and traces of 2-tert-butylpyrrole were found as by-products.

EXAMPLE 10

The process was carried out essentially as in Example 8, the potassium oximate solution used being a solution prepared from 13.5 g (100 mmol) of acetophenone oxime, 6 g (110 mmol) of KOH and 150 ml of DMSO. 100 ml of petroleum ether were added to the solution. The acetylene pressure was 14 bar, and the reaction time was 1 hour at 60° C. The conversion of acetophenone oxime was 79.8%, the yield of O-vinylacetophenone was 40.2%, based on the amount of oxime reacted. 4.0% of 2-phenypyrrole were found as by-product.

EXAMPLES 11 and 12

As describe din Example 10, substituted acetophenones were reacted to give the corresponding vinyl ether. The experimental data and results are given in the table below. The reaction time in each case was 1 hour and the reaction temperature was 60° C.

| Example | Oxime g (mmol) | KOH g (mmol) | DMSO ml | Petroleum ether ml | Yield % | Conversion |
|---|---|---|---|---|---|---|
| 11 | 8.2 (50) | 3 (54) | 75 | 50 | 46.0 | 64.4 |
| 12 | 4.1 (25) | 1.5 (27) | 38 | 25 | 59.0 | 70.5 |

The yield is again based on reacted oxime. The oxime used in Example 11 was 4-ethylacetophenone oxime, and the oxime used in Example 12 was 4-methoxyacetophenone oxime. In both cases, the DMSO layer which was separated off was extracted again with ether.

We claim:

1. A process for the preparation of vinyloxime ethers of the formula I

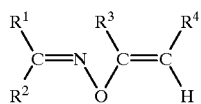 (I)

by reacting a ketoxime of the formula II

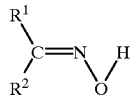 (II)

with an alkyne of the formula III

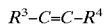 (III)

where $R^1$ and $R^2$ are identical or different and are alkyl or aryl radicals, $R^3$ is hydrogen, an alkyl or aryl radical, and $R^4$ is a radical having the meaning of $R^3$, which may be different than $R^3$, or is a hydroxyalkyl radical, in a superbasic polar organic solvent in the presence of a strong base, which comprises carrying out the reaction at from 50 to 100° C. and separating off the resulting vinyloxime ether by carrying out the reaction in the presence of an inert nonpolar organic solvent which is immiscible with the superbasic polar organic solvent and which is a good solvent for the resulting O-vinyloxime ether, such that the resulting vinyloxime ether stays in contact with the other constituents of the reaction mixture for only a short time so that it is unable to decompose or react to give secondary products to a substantial extent.

2. A process as claimed in claim 1, wherein the nonpolar organic solvent is a hydrocarbon.

3. A process as claimed in claim 2, wherein the hydrocarbon is a aliphatic hydrocarbon boiling in the range from 30 to 200° C.

4. A process as claimed in claim 1, wherein $R^1$ and $R^2$ are alkyl radicals having from 1 to 4 carbon atoms.

5. A process as claimed in claim 1, wherein $R^3$ and $R^4$ are hydrogen.

6. A process as claimed in claim 1, wherein the strong base is an alkali metal hydroxide.

7. A process as claimed in claim 1, wherein the reaction is carried out under increased pressure.

* * * * *

UNITED STATES PATENT AND TRADEMARK OFFICE
CERTIFICATE OF CORRECTION

PATENT NO. : 6,313,347 B1
DATED : November 6, 2001
INVENTOR(S) : Preiss et al.

Page 1 of 1

It is certified that error appears in the above-identified patent and that said Letters Patent is hereby corrected as shown below:

<u>Title page,</u>
Item [73], the Assignee's information should read:
[73] Assignee: BASF Aktiengesellschaft,
Ludwigshafen (DE)

Signed and Sealed this

Twelfth Day of March, 2002

Attest:

*Attesting Officer*

JAMES E. ROGAN
*Director of the United States Patent and Trademark Office*